United States Patent
Guy et al.

(10) Patent No.: US 6,936,749 B1
(45) Date of Patent: Aug. 30, 2005

(54) NONSYMBIOTIC PLANT HEMOGLOBINS TO MAINTAIN CELL ENERGY STATUS

(75) Inventors: Phillip Guy, Geneva, IL (US); Stephen Duff, Winnipeg (CA); Nie Xianzhou, Winnipeg (CA); Robert Hill, Winnipeg (CA); Douglas Durnin, Winnipeg (CA); Aleksander Sowa, Warsaw (PL)

(73) Assignee: The University of Manitoba, Manitoba (CA)

( * ) Notice: Subject to any disclaimer, the term of this patent is extended or adjusted under 35 U.S.C. 154(b) by 0 days.

(21) Appl. No.: 09/720,206

(22) PCT Filed: Jun. 24, 1999

(86) PCT No.: PCT/CA99/00587

§ 371 (c)(1),
(2), (4) Date: May 3, 2001

(87) PCT Pub. No.: WO00/00597

PCT Pub. Date: Jan. 6, 2000

Related U.S. Application Data

(60) Provisional application No. 60/106,638, filed on Nov. 2, 1998, and provisional application No. 60/090,929, filed on Jun. 26, 1998.

(51) Int. Cl.[7] .................. C12N 15/29; C12N 15/82; A01H 5/00
(52) U.S. Cl. ............. 800/298; 800/278; 800/290; 536/23.1; 536/23.2; 536/23.6
(58) Field of Search ................. 800/278, 298, 800/290, 317.3; 536/23.1, 23.2, 23.6; 435/69.1

(56) References Cited

U.S. PATENT DOCUMENTS 5,959,187 A * 9/1999 Bailey et al. ............ 800/317.3
6,372,961 B1 * 4/2002 Tarczynski et al. ......... 800/278

FOREIGN PATENT DOCUMENTS

WO    WO 98/12913    4/1998
WO    WO/98/12913  * 4/1998

OTHER PUBLICATIONS

Dolferus R. et al. Annals of Botany, Jan. 1997; vol. 79, Supplement A; pp. 21–31.*
Goodenough U., Genetics; 1978, 2nd ed., Holt, Rinehart and Winston; pp. 771–772.*
(Dordas C. et al., Annals of Botany, 2003, vol. 91; pp. 173–178.*
Taylor, E. et al. Plant Molecular Biology, 1994; vol. 24, pp. 853–862.*
Hartl D. et al., Genetics: Analysis of Genes and Genomes; 5th Ed., Jones and Bartlett Publishers.*
Andersson et al. A new hemoglobin gene from soybean: A role for hemoglobin in all olants. Proc.Natl.Acad.Sci.USA., vol. 93, pp. 5682–5687, 1996.
Jacobsen–Lyon et al. Symbiotic and nonsymbiotic haemoglobin genes of *Casuarina glauca*. Plant Cell, vol. 7:213–223, 1995.*

Sowa et al. Altering hemoglobin levels changes energy status in maize cells under hypoxia. Proc.Natl.Acad. Sci.USA., vol. 95: 10317–10321, 1998.*
Giovanni Antonini et al., "Cyanide dissociation from the hemoglobin of *Parascaris equorum*", Biochimica et Biophysica Acta, (1994), vol. 1205, p. 252–257.
Karin Jacobsen–Lyon et al., "Symbiotic and Nonsymbiotic Hemoglobin Genes of *Casuarina glauca*", The Plant Cell, Feb. 1995, vol. 7, p. 213–223.
Aleksander W. Sowa et al., "Altering hemoglobin levels changes energ status in maize cells under hypoxia", *Proceedings of the National Academy of Sciences USA*, Aug. 1998, vol. 95, p. 10317–10321.
Raul Arredondo–Peter et al., " Gene Cloning, Analysis, and O2–Binding Kinetics of a Recombinant Protein Synthesized in *Escherichia coli*", Plant Physiology, (1997) 115, p. 1259–1266.
S.–C. Liu et al., "Cloning and expression of the *Vitreoscilla* hemoglobin gene in pseudomonads: effects on cell growth", Appl Microbiol Biotechnol 1995, vol. 44, pp 419–424.
Meenal Joshi and Kanak L. Dikshit, "Oxygen dependent regulation of *Vitreoscilla* globin gene: evidence for positive regulation by fnr", 1994, *Biochemical and Biophysical Research Communications* 202: 535–542.

(Continued)

Primary Examiner—Amy J. Nelson
Assistant Examiner—Russell Kallis
(74) Attorney, Agent, or Firm—Foley & Lardner LLP

(57) ABSTRACT

Nonsymbiotic hemoglobins are broadly present across evolution; however, the function of these proteins is unknown. Cultured maize cells have been transformed to constitutively express a barley hemoglobin gene in either the sense (HB$^+$) or antisense (HB$^-$) orientation. Hemoglobin protein in the transformed cell lines was correspondingly higher or lower than in wild type cells under normal atmospheric conditions. Limiting oxygen availability, by placing the cells in a nitrogen atmosphere for 12 hours, had little effect on the energy status of cells constitutively expressing hemoglobin, but had a pronounced effect on both wild type and HB$^-$ cells, where ATP levels declined by 27% and 61% respectively. Energy charge was relatively unaffected by the treatment in HB$^+$ and wild type cells, but was reduced from 0.91 to 0.73 in HB$^-$ cells suggesting that the latter were incapable of maintaining their energy status under the low oxygen regime. Similar results were observed with *P. aeruginosa* cells transformed with an Hb expression vector. It is suggested that nonsymbiotic hemoglobins act to maintain the energy status of cells in low oxygen environments and that they accomplish this effect by promoting glycolytic flux through NADH oxidation, resulting in increased substrate level phosphorylation. Nonsymbiotic hemoglobins are likely ancestors of an early form of hemoglobin that sequestered oxygen in low oxygen environments, providing a source of oxygen to oxidize NADH to provide ATP for cell growth and development. This in turn suggests that cells containing increased levels of Hb protein will survive longer under low oxygen tension or high energy demand.

20 Claims, 13 Drawing Sheets

OTHER PUBLICATIONS

Christensen et al, Maize polyubiquitin genes: structure, thermal perturbation of expression and transcript splicing, and promoter activity following transfer to protoplasts by electroporation, 1992, *Plant Molecular Biology* 18: 675–689.

Andrews and Pomeroy, Metabolic Acclimation to Hypoxia in Winter Cereals, 1989, *Plant Physiol* 91: 1063–1068.

Xia and Roberts, Regulation of $H^+$ Extrusion and Cytoplasmic pH in Maize Root Tips Acclimated to a Low–Oxygen Environment, 1996, *Plant Physiol* 111:227–233.

Taylor et al, A cereal haemoglobin gene is expressed in seed and root tissues under anaerobic conditions, 1994, *Plant Molecular Biology* 24: 853–862.

Hanson and Jacobsen, Control of Lactate Dehydrogenase, Lactate Glycalysis, and α–Amylase by $O_2$ Deficit in *Barley Aleurone* Layers, 1984, *Plant Phyiol* 75: 566–572.

Becker et al, Fertile transgenic wheat from microprojectile bombardment of scutellar tissue, 1994, *The Plant Journal* 5: 299–307.

Johnson et al, Hypoxic Induction of Anoxia Tolerance in Root Tips of *Zea mays,* 1989, *Plant Physiol* 91: 837–841.

Andersson et al, A new hemoglobin gene from soybean: A role for hemoglobin in all plants, 1996, *PNAS* 93: 5682–5687.

Kaeppler et al, Silicon carbide fiber–mediated stable transformation of plant cells, 1992, *Theor Appl Genet* 84: 560–566.

Appleby, The origin and functions of haemoglobin in plants, 1992, *Sci Progress Oxford* 76: 365–398.

Wittenberg and Wittenberg, Mechanisms of cytoplasmic hemoglobin and myoglobin function, 1990, *Annu Rev Biophys Biophys Chem* 19: 217–241.

Xia and Saglio, Lactic Acid Efflux as a Mechanism of Hypoxic Acclimation of Maize Root Tips to Anoxia, 1992, *Plant Physiol* 100: 40–46.

Duff et al. Expression, Purification, and Properties of Recombinant Barley (*Hordeum* sp.) Hemoglobin, 1997, *JBC*: 16746–16752.

Nie and Hill, Nitochondrial Respiration and Hemoglobin Gene Expression in Barley Aleurone Tissue, 1997, *Plant Physiol* 114: 835–840.

Murashige and Skoog, A Revised Medium for Rapid Growth and Bio Assays with Tobacco Tissue Cultures, 1962, *Physiologica Plantarum* 15: 473–497.

Heslop–Harrison et al, The evaluation of pollen quality, and a further appraisal of the fluorochromatic (FCR) test procedure, 1984, *Theor Appl Genet* 67: 367–375.

Trevaskis et al, Two hemoglobin genes in *Arabidopsis thaliana:* The evolutionary orgins of leghemoglobins, 1997, *PNAS* 94: 12230–12234.

Andersson et al, A new hemoglobin gene from soybean: A role for hemoglobin in all plants, 1996, *PNAS* 93: 5682–5687.

\* cited by examiner

A. pAS1 (Sense)

B. pAS2 (Anti-sense)

NONSYMBIOTIC PLANT HEMOGLOBINS TO MAINTAIN CELL ENERGY STATUS

This application is a National Phase entry of PCT CA99/00587, having an international filing date of Jun. 24, 1999 and this application claims priority under 35 USC §119(e) to U.S. Ser. No. 60/106,638, filed Nov. 2, 1998 and to U.S. Ser. No. 60/090,929, filed Jun. 26, 1998.

The present invention relates generally to the field of expression vectors and transgenic organisms.

BACKGROUND OF THE INVENTION

Hemoglobins are widespread throughout the biosphere (Wittenberg and Wittenberg, 1990. *Annu Rev Biophys Biophys Chem* 19:217–241). They are found in a broad range of organisms from bacteria, through unicellular eukaryotes, to plants and animals, suggesting that they predate divergence of life into plant and animal forms. Plant hemoglobins have been classified into symbiotic and nonsymbiotic types (Appleby. 1992, *Sci Progress* 70:365–398): symbiotic hemoglobins are found in plants that are capable of participating in microbial symbioses, where they function in regulating oxygen supply to nitrogen fixing bacteria; nonsymbiotic hemoglobins have only recently been discovered and are thought to be the evolutionary predecessors of the more specialized symbiotic leghemoglobins. The ubiquitous nature of nonsymbiotic hemoglobins is evidenced by their broad presence across the plant kingdom (Appleby, 1985, *Nitrogen Fixation and $CO_2$ Metabolism,* eds. Ludden and Bums, pp. 41–51) and the widespread presence and long evolutionary history of plant hemoglobins suggest a major role for them in the life of plants.

Specifically, plant hemoglobins have been known to exist in the root nodules of legumes for almost 60 years (Kubo, 1939, *Acta Phitochem* 11:19–200; Keilen and Wang, 1945, *Nature* 155:227–229). Over the years, hemoglobins have been positively identified in three non-leguminous dicotyledonous plants; *Parasponia andersonil, Tream tomentosa,* and *Casuarina glauca* (Appleby et al., 1983, *Science* 220:951–954; Bogusz et al., 1988, *Nature* 331:178–180; Kort et al., 1998, *FEBS Lett* 180:55–60). Recently, an Hb cDNA from badey was isolated and the gene was demonstrated to be expressed in seed and root issues under anaerobic conditions (Taylor et al., 1994. *Plant Mol Biol* 24:853–862), providing further evidence to support the contention that plant hemoglobins have a common origin (Landsmann et al., 1986. *Nature* 324:166–168). Since Hb has now been demonstrated to occur in two of the major divisions of the plant kingdom, it is likely that an Hb gene is present in the genome of all higher plants (Brown et al., 1984, *J Mol Evol* 21:19–32; Bogusz et al., 1988; Appleby, 1992, *Sci Progress* 76:365–398; Taylor et al., 1994; Andersson et al., 1996, *Proc Natl Acad Sci USA* 93:427–431; Hardison, 1996, *Proc Natl Acad Sci USA* 93:5675–5682).

Very little, however, is known about the function of Hb, although it has been proposed that nonsymbiotic hemoglobins may act either as oxygen carriers to facilitate oxygen diffusion, or oxygen sensors to regulate expression of anaerobic proteins during periods of low oxygen supply. The proteins from barley (Duff et al, 1997, *J. Biol Chem* 272:16746–16752) and rice (Arrendondo-Peter et al, 1997, *Plant Physiol* 115:1259–1266) and AHB1 from *Arabidopsis* (Trevaskis et al, 1997, *Proc Natl Acad Sci* 94:12230–12234) have been shown to have high oxygen avidity, with dissociation constants for oxyhemoglobin of 2.86 nM, 0.55 nM and 1.6 nM respectively, resulting in conditions whereby the free protein will remain oxygenated at oxygen concentrations far below those at which anaerobic processes are activated. Thus, while roles for Hb in the facilitated diffusion and sensing of oxygen have been proposed (Appleby, 1992), it is unlikely that these hemoglobins would function as either facilitators of oxygen diffusion or sensors of oxygen, unless the oxygen avidity was modified by interaction with another component within the cell. Thus, while Hb or Hb related proteins are found in all divisions of living organisms, their function has not been well defined.

Herein, it is shown that nonsymbiotic hemoglobins function to maintain the energy status of cells exposed to low oxygen tensions and that this property may be a common feature throughout evolution, either during exposure to hypoxia or under high energy demand.

SUMMARY OF THE INVENTION

According to one aspect of the invention there is provided a recombinant expression system capable, when transformed into an organism, of expressing a gene encoding a nonsymbiotic hemoglobin, which system comprises a nucleotide sequence encoding said nonsymbiotic hemoglobin operably linked to control sequences effective in said organism.

The control sequences may include a strong constitutive promoter.

The nonsymbiotic hemoglobin may be barley hemoglobin.

The organism may be a plant. The plant may be maize. Preferably, the promoter is maize ubiquitin promoter.

The organism may be a bacteria. The bacteria may be an obligate aerobe. The obligate aerobe may be *P. aeruginosa*.

According to a second aspect of the invention, there are provided cells transformed with any one of the expression systems described above.

According to a third aspect of the invention, there is provided a transgenic organism whose genome has been modified to contain the expression system described above.

According to a fourth aspect of the invention, there is provided a method of increasing tolerance to hypoxic conditions comprising:

providing an organism having increased cellular levels of an oxygen-binding protein having a low dissociation constant for oxygen; and placing the organism under hypoxic conditions, wherein the oxygen-binding protein acts to maintain cellular energy status during the hypoxic conditions by making oxygen available for cellular metabolism at low oxygen tension.

According to a fifth aspect of the invention, there is provided a method of lowering the level of fermentation products in an organism comprising:

providing an organism having increased cellular levels of an oxygen-binding protein having a low dissociation constant for oxygen; and reducing the level of fermentation products in the cells of the organism by maintaining cell energy status such that fermentation is bypassed.

According to a sixth aspect of the invention, there is provided a method of maintaining cellular metabolism under hypoxic conditions comprising:

providing an organism having increased cellular levels of an oxygen-binding protein having a low dissociation constant for oxygen; and placing the organism under hypoxic conditions, wherein the oxygen-binding protein acts to maintain cellular metabolism status by providing oxygen for cellular metabolism.

According to a seventh aspect of the invention, there is provided a method of increasing oxygen uptake of an organism comprising:

providing an organism having increased cellular levels of an oxygen-binding protein having a low dissociation constant for oxygen; and exposing the organism to an oxygen-containing environment, wherein the increased cellular levels of the oxygen-binding protein results in increased oxygen uptake.

According to an eighth aspect of the invention, there is provided a method of improving the agronomic properties of a plant comprising:

providing a plant having increased cellular levels of an oxygen-binding protein having a low dissociation constant for oxygen; and growing the plant.

The improved agronomic properties may include germination, seedling vigour, reduced cellular levels of fermentation products, increased oxygen uptake, and increased tolerance to hypoxic conditions.

According to a ninth aspect of the invention, there is provided a method of performing skin grafts comprising:

isolating skin cells from a patient;

transfecting the skin cells with an expression system comprising a nucleotide sequence encoding an oxygen binding protein having a low dissociation constant for oxygen operably linked to control sequences effective in skin cells;

culturing the skin cells such that the oxygen binding protein is expressed; and grafting the skin cells onto a region of skin tissue attached to the patient.

According to a tenth aspect of the invention, there is provided a method of transplanting an organ from a donor to a recipient comprising:

providing an organ for transplant;

infusing the organ with an oxygen binding protein having a low dissociation constant for oxygen, thereby improving oxygen supply to the organ; and transplanting the organ into the recipient.

The oxygen binding protein having a low dissociation constant for oxygen described in the above methods may be a nonsymbiotic hemoglobin. The nonsymbiotic hemoglobin may be barley hemoglobin.

According to an eleventh aspect of the invention, there is provided a method of selecting seeds for breeding to produce seed lines having desirable characteristics comprising:

providing a representative seed of a given seed line;

growing the seed such that the seed germinates;

isolating an extract from the seed;

measuring levels of hemoglobin expression within the extract; and selecting or rejecting the seed for further breeding based on the hemoglobin levels.

According to a twelfth aspect of the invention there is provided a method of determining if a seed is germinating comprising:

providing a seed suspected of germinating;

isolating a extract from the seed; and measuring levels of hemoglobin expression within the extract, wherein high levels of hemoglobin expression indicate that the seed is germinating.

One embodiment of the invention will now be described in conjunction with the accompanying figures in which:

Figure 1:
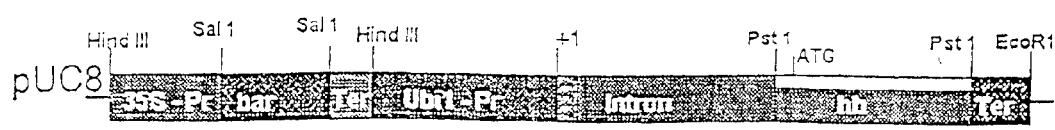
FIG. 1 is a schematic diagram summarizing the structures of pAS1 and pAS2 respectively.
Figure 1:
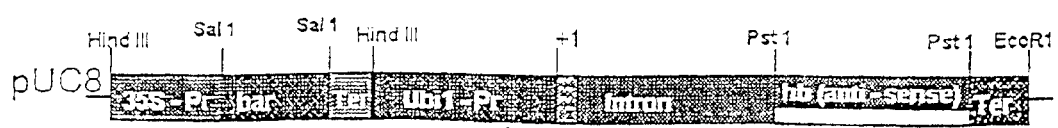

Table 1 is a summary of measurements of energy charge and total adenylates in maize cells before and after exposure to a nitrogen atmosphere for 12 hours.

Table 2 is a summary. of $A_{600}$ measurements of transformed and untransformed E. coli and P. aeruginosa cells grown aerobically or anaerobically. Measurements are the averages of two separate determinations which did not vary by more than 15%.

Table 3 is a summary of ATP measurements of transformed and untransformed E. coli and P. aeruginosa cells grown aerobically and anaerobically. Measurements are the results of duplicate. assays from three separate experiments. Standard error in all cases was no greater than 10%.

DETAILED DESCRIPTION

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Expression plasmids containing DNA encoding a nonsymbiotic hemoglobin were constructed. These plasmids also included a strong constitutive promoter and a selectable marker compatible with the specific host organisms such that when these plasmid constructs were transformed into the host organisms, the constructs expressed elevated levels of Hb protein compared to wild type cells. In all cases, the transformed cells had an elevated level of ATP. This strongly suggests that nonsymbiotic hemoglobin functions in maintaining ATP levels and is involved in primary energy metabolism. Thus, cells engineered to express a higher level of Hb will survive longer under low oxygen tension or high energy demand. In other words, the cells maintain vigour and hardiness under stressful conditions and can better adapt to varying growth conditions. That is, transformed crop plants containing elevated levels of the nonsymbiotic hemoglobin gene may exhibit increased crop yields due to the ability of the plant to more effectively survive periods of flooding, the ability of the seed and seedling to develop more vigorously under adverse germination and/or growth conditions, and the ability of winter crops to survive ice cover more effectively. Furthermore, given that the effect of nonsymbiotic hemoglobin on cell energy status is seen in both bacteria and plants, it seems likely that this phenomenon is universal. This would in turn mean that nonsymbiotic hemoglobins have potential applications in a number of medical procedures. For example, skin cells from burn victims are frequently cultured for transplantation back to the burn victim. Given that oxygen supply is a limiting factor for growth and survival of the transplanted skin grafts, skin cells transfected with nonsymbiotic hemoglobin may possess improved growth and survival. Similarly, oxygen supply is also a limiting factor in other medical procedures, for example, organ transplants. That is, it is likely that organs possessing nonsymbiotic hemoglobins may have enhanced survival following transplant. Furthermore, the hemoglobin gene itself is shown to be expressed at time of germination, meaning that the hemoglobin gene may be used as a marker for germination and also as a marker for breeding. That is, levels of hemoglobin in specific seed lines may be used to select seeds for developing progeny seeds capable of expressing either higher or lower levels of hemoglobin.

In one embodiment, expression plasmids containing DNA encoding barley hemoglobin in both the sense and anti-sense orientation were constructed. The plasmids also included the maize ubiquitin promoter, and a selectable marker for selection of transformants, in this embodiment, a herbicide resistance gene (Bar), conferring resistance to glufosinate ammonium. The plasmids were transformed into cultured maize cells of the Black Mexican Sweet (BMS) variety, producing a cell line containing the sense plasmid (HB$^+$) and a cell line containing the antisense plasmid (HB$^-$).

When grown in an air environment, the HB$^+$ and HB$^-$ cells did not differ significantly from wild-type BMS cells in terms of growth rate, oxygen consumption or cellular ATP levels. However, when grown under a nitrogen atmosphere, ATP levels in the HB$^+$ cells remained essentially the same as those observed under normal atmosphere conditions while ATP levels dropped significantly in wild-type and HB$^-$ cells.

Analysis of ATP levels in all three cell lines under a nitrogen atmosphere following treatment with Antimycin A (which blocks mitochondrial electron transport) indicated that the increase in ATP in HB$^+$ cells was not cytochrome-mediated. Furthermore, measurements of $CO_2$ evolution and alcohol dehydrogenase activity in HB$^+$ cells suggested lower ethanolic fermentation rates in this cell line.

These data indicate that over-expression of nonsymbiotic hemoglobins helps maintain the energy status of cells grown at low oxygen tensions. This in turn has several possible applications, as cells capable of maintaining energy status at low oxygen tensions would have, for example, increased tolerance to a low oxygen atmosphere, improved germination rates and seedling vigour, increased ability to maintain cellular metabolism at low oxygen tension, reduced levels of fermentation products within the cells due to lowered alcohol dehydrogenase activity, increased oxygen uptake under low oxygen tension and increased tolerance to hypoxic conditions such as, for example, ice encasement, flood and growth in compacted soil.

EXAMPLE I

Plant Cell Cultures

Black Mexican Sweet (BMS) (wild-type), HB$^+$ and HB$^-$ maize cells were cultured in 250 ml flasks as cell suspensions in 50 ml of MS medium (Murashige and Skooge, 1962, *Physiol Plant* 15:473–497) macro and micro elements supplemented with thiamine 0.5 mg/liter, L-asparagine 150 mg/liter, 2,4-dichlorophenoxyacetic acid 2 mg/liter and sucrose 20 g/liter. Cultures were shaken at 150 rpm at 25° C. Cells were subcultured every 7 days. Nitrogen treatment was applied by replacing air in culture flasks with nitrogen and closing the flasks with rubber stoppers, otherwise culture flasks were closed with caps allowing for free exchange of air. Antimycin A was added as a 27 mM stock solution in 2-propanol to give a final concentration of 0.2 mM. Cell samples were collected by filtration. Cell samples used for adenylate measurements were immediately frozen in liquid nitrogen and stored at −80° C. until used.

EXAMPLE II

Construction of Plant Expression Vectors

SalI/NotI digested and end-filled barley hemoglobin cDNA was cloned into BamHI digested and end-filled pAHC17 plasmid (Christensen and Quail, 1996, *Transgenic Research* 5:213–218) in sense and antisense orientation to generate pAS1 (sense) and pAS2 (antisense) plasmids. An EcoRI digested, end-filled with synthetic HindIII linker, 1.35 kb 35S promoter —bar gene— 35S terminator fragment from pDB1 (Becker et al, 1994, *Plant J* 5:299–307) was inserted into HindIII digested pAS1 and pAS2, as described below.

EXAMPLE III

Plant Cell Transformation and Selection

A silicon carbide fibres-mediated transformation system was used as described in Kaeppler et al, 1992, *Theor App Genet* 84:560–566 to transform BMS maize cells with pAS1 and pAS2 vectors. Resistant colonies were selected on culture medium solidified with 0.2% Phytagel™ (Sigma) and supplemented with glufosinate ammonium at a concentration of 5 mg/liter.

EXAMPLE IV

Plant Protein Immunoblots

SDS gel electrophoresis, protein transfer to nitrocellulose membrane and antibody detection were performed according to standard Bio-Rad protocol (Bio-Rad bulletin 1721). Hemoglobin protein in transformed lines was detected by immunoblots; using a polyclonal antibody raised against barley recombinant hemoglobin. Protein concentration was calculated by densitometric comparison of immunoblots (in four repetitions) with a standard curve of known concentrations of recombinant hemoglobin using a Sharp Diversity 1 PDI-3250E Scanner™.

EXAMPLE V

Measurement of Plant Growth Parameters

Culture growth was measured by sedimentation in 25 ml graduated pipettes. Adenylates were extracted in 1N perchloric acid from frozen cell samples at −10° C. and ATP, ADP and AMP assayed spectrophotometrically by established protocols as described in Lowry and Passonneau, 1972, *A Flexible System of Enzymatic Analysis*, Academic Press: New York.

Alcohol dehydrogenase activity was measured in the ethanol-acetaldehyde direction in fresh cell extracts. Enzyme extraction and spectrophotometric measurements were performed as described in Hanson and Jacobsen, 1984, *Plant Physiol* 75:566–572.

For measurements of $CO_2$ evolution from cell cultures, 1 ml gas samples were collected with an air tight syringe, from stoppered culture flasks, and analyzed by gas chromatography (Shimadzu GC-8AIT™).

Oxygen uptake was measured polarographically with an $O_2$ electrode (Rank Brothers, Cambridge, UK) for 5 to 30 minutes. The incubation cell contained 2 ml of culture medium, 0.2 ml (sedimented cell volume) of cells. In some measurements, 0.2 mM Antimycin A was added, as described below.

EXAMPLE VI

Effect of Nonsymbiotic Hemoglobin on Plant Cell Energy Status

Figure 2:
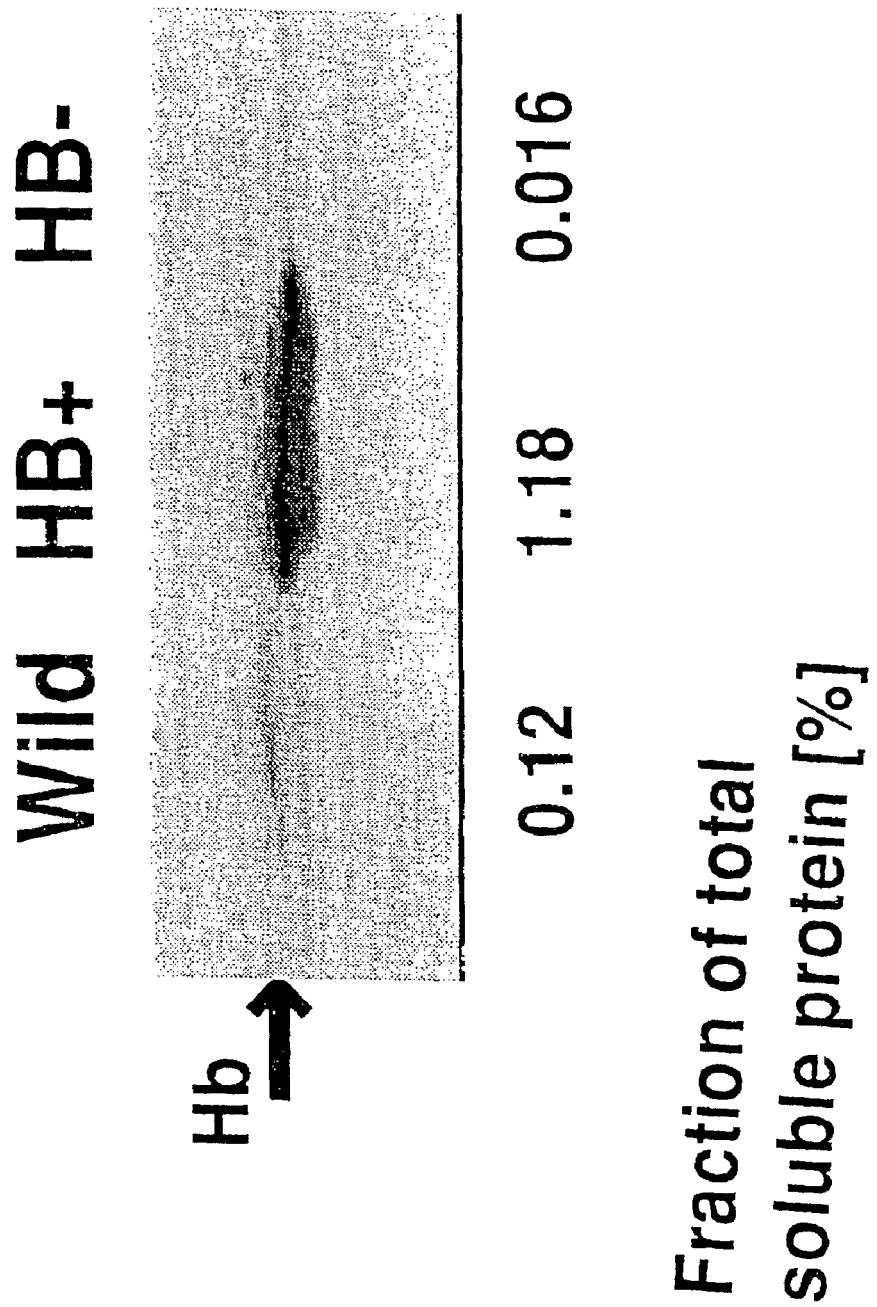
FIG. 2 is the protein immunoblot analysis of hemoglobin expression in wild-type (BMS), $HB^+$ and $HB^-$ maize cell lines with recombinant barley hemoglobin-specific antibody.

As noted above, cultured maize cells of the Black Mexican Sweet (BMS) variety were transformed with a barley hemoglobin gene to observe the effect of increasing or decreasing hemoglobin expression on cell metabolism. Specifically, transformation vectors, shown in FIG. 1, were prepared containing the open reading frame of a barley hemoglobin cDNA in sense and antisense orientations, which were placed under the control of a strong constitutive promoter, in this embodiment, the maize ubiquitin (Ubi1) promoter. A herbicide resistance gene (Bar), conferring resistance to glufosinate ammonium, was cloned head to tail with the hemoglobin gene constructs to enable selection of transformed cell lines. Twenty-four independently transformed sense (pAS1) and thirty-eight anti-sense (pAS2) lines were obtained. Transformation was confirmed by Southern blbt analysis and PCR. A sense line ($HB^+$) expressing hemoglobin at levels 10 fold higher than wild type (BMS) and an antisense line ($HB^-$) with 10 times lower expression of hemoglobin than BMS, as shown in FIG. 2, were selected for further studies, as described below.

Figure 3:
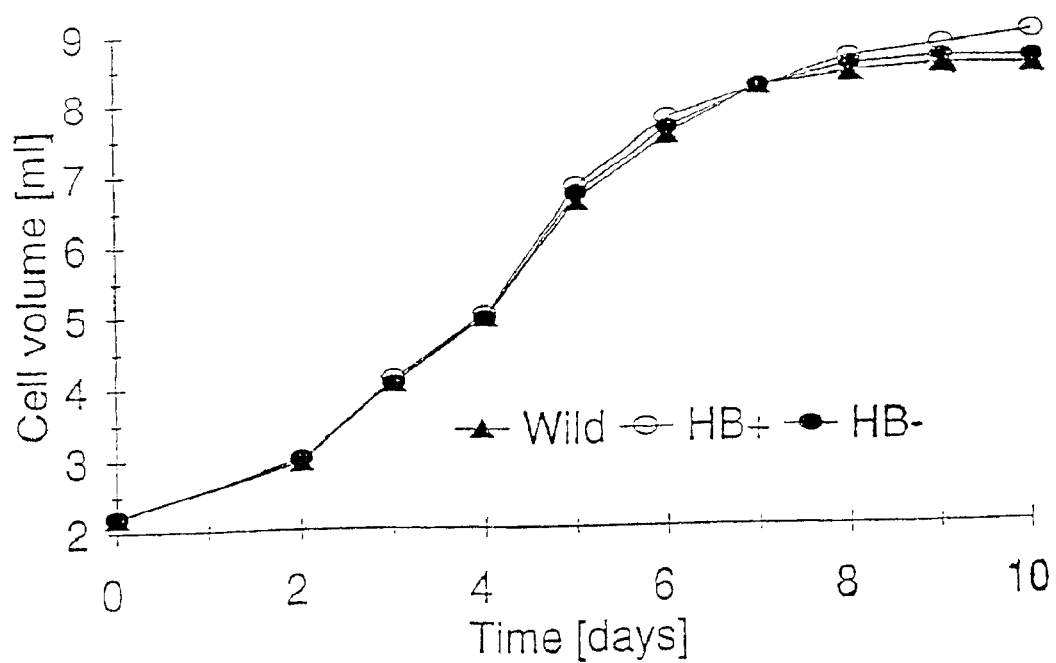
FIG. 3 is a graph of the growth rate of wild-type (BMS), $HB^+$ and $HB^-$ maize cell lines under normal atmospheric conditions.
Figure 4:
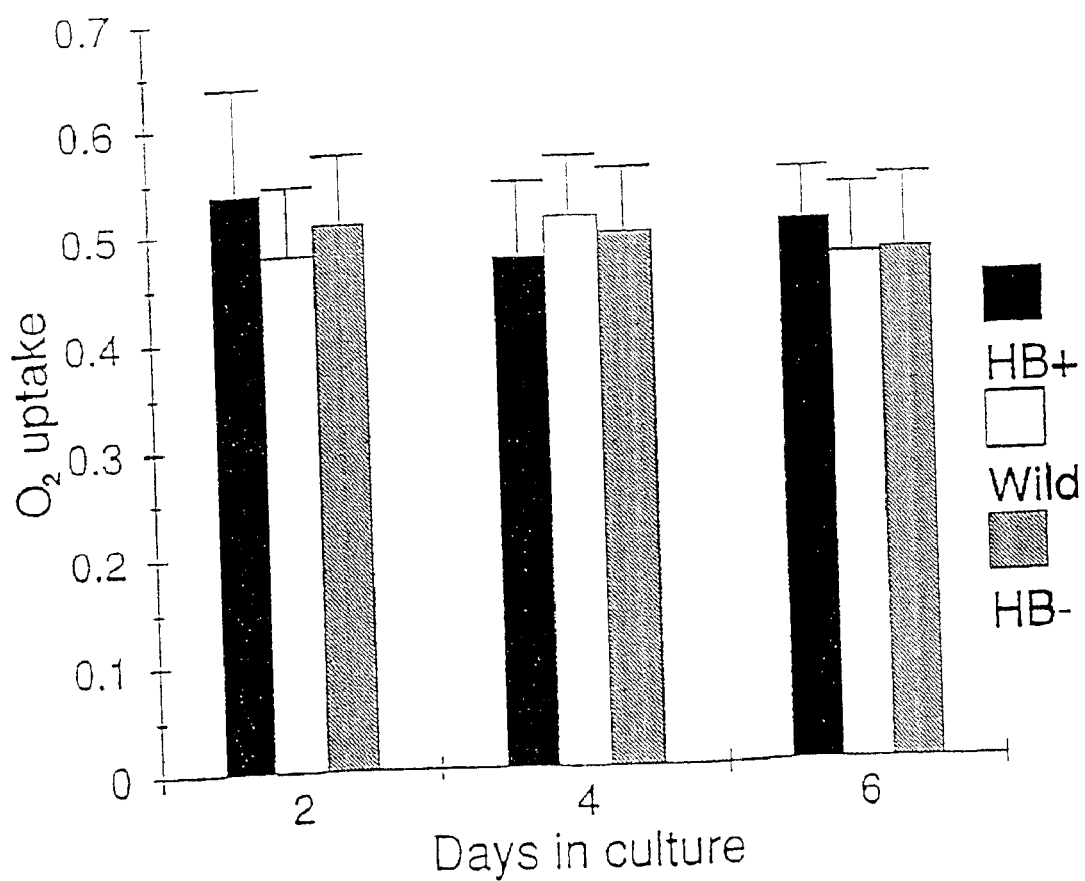
FIG. 4 is a bar graph comparison of oxygen uptake by maize wild-type (BMS), $HB^+$ and $HB^-$ cells.
Figure 5:
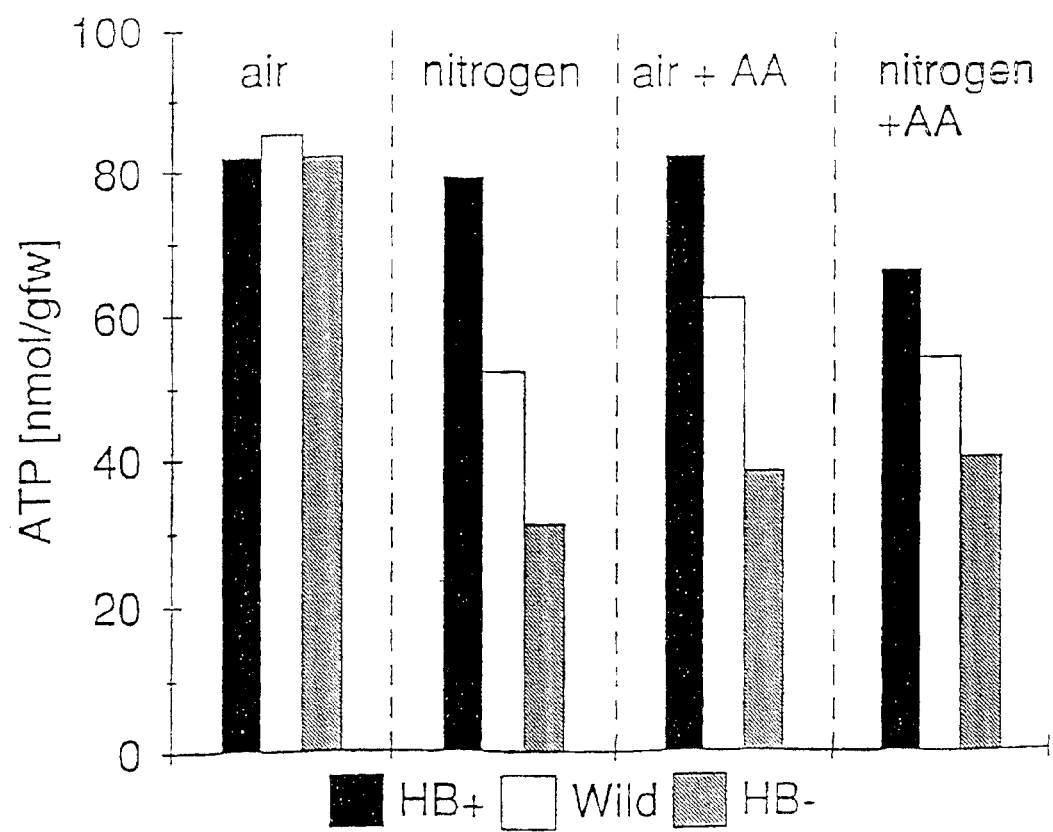
FIG. 5 is a bar graph comparison of ATP levels in wild-type (BMS), $HB^+$ and $HB^-$ maize cells grown under normal atmospheric conditions, after 12 hours of treatment with nitrogen, under normal atmospheric conditions following treatment with Antimycin A and after 12 hours of treatment with nitrogen following treatment with Antimycin A.

The three cell lines, grown in an air environment, did not differ significantly from one another with respect to culture growth rates, as shown in FIG. 3, and consumption of oxygen, as shown in FIG. 4. Furthermore, steady state ATP levels were essentially the same in the three types of cells, as shown in FIG. 5. However, after incubation of the cells for a further 12 hours under an atmosphere of nitrogen gas, significant differences were observed in the ATP levels of the cell types. Specifically, the level of ATP was highest in $HB^+$ cells, being only marginally lower than under normal atmospheric conditions while ATP levels in wild type (BMS) cells were 27% lower than $HB^+$ cells and ATP levels in $HB^-$ cells were 61% lower than $HB^+$ cells. Differences in energy charge and total adenylates were also observed in cells exposed to nitrogen atmospheres, as summarized in Table 1. As can be seen, energy charge was relatively the same in all three cell types under normal atmospheric conditions and in BMS and $HB^+$ cell lines after 12 hours of a nitrogen atmosphere. $HB^-$ cells, on the other hand, were unable to maintain energy charge during the 12 hour exposure to a nitrogen atmosphere. Total adenylates remained the same in all three cell lines under atmospheric conditions and in $HB^+$ cells in a nitrogen atmosphere; however, in BMS and $HB^-$ cells, the total adenylates declined by about 35 percent.

From this, it is evident that determining what part of the cell's metabolism contributes to this increased ability to maintain energy status in the presence of hemoglobin is critical to understanding the role of nonsymbiotic hemoglobin. To examine the possibility that hemoglobin might provide oxygen to generate ATP via cytochrome-mediated respiratory processes, Antimycin A (0.2 mM), which blocks mitochondrial electron transport in the span from cytochrome b to c and has been shown to induce hemoglobin expression in aleurone layers (Nie and Hill, 1997, *Plant Physiol* 114:835–840) was used. Antimycin A inhibited 80% of the oxygen uptake by maize cells within 30 minutes of treatment. After 12 hours exposure to Antimycin A in an air environment, ATP levels in the three cell types were similar to those of untreated cells after 12 hours under a nitrogen atmosphere, as shown in FIG. 5. However, upon placing Antimycin A-treated cells in a nitrogen atmosphere for 12 hours, the cell lines all showed decreases in ATP but, consistent with the previous experiments, the levels of ATP decreased in the order $HB^+$, BMS, and $HB^-$. This provides evidence that the increase in ATP brought about by the presence of hemoglobin was not the result of cytochrome-mediated mitochondrial respiration. It is also unlikely that the increased ATP is the result of oxyhemoglobin supporting mitochondrial alternative oxidase activity, which would increase substrate phosphorylation through glycolysis.

Figure 6:
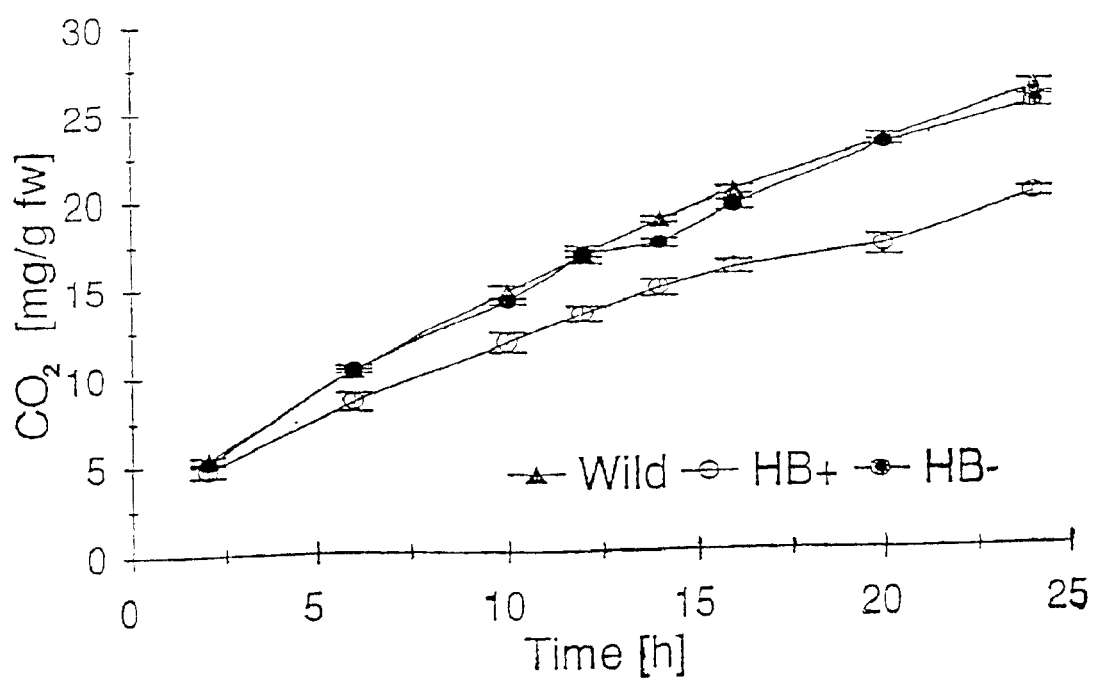
FIG. 6 is a bar graph comparison of $CO_2$ evolution by maize cells cultured under a nitrogen atmosphere.

Furthermore, as shown in FIG. 6, $CO_2$ evolution from hypoxic $HB^+$ cells was 20 to 30% lower than $CO_2$ levels evolved from BMS or $HB^-$ cells, which would not be anticipated if the Krebs cycle was being maintained through alternative oxidase activity.

EXAMPLE VII

Plant Cell Alcohol Dehydrogenase Levels

Figure 7:
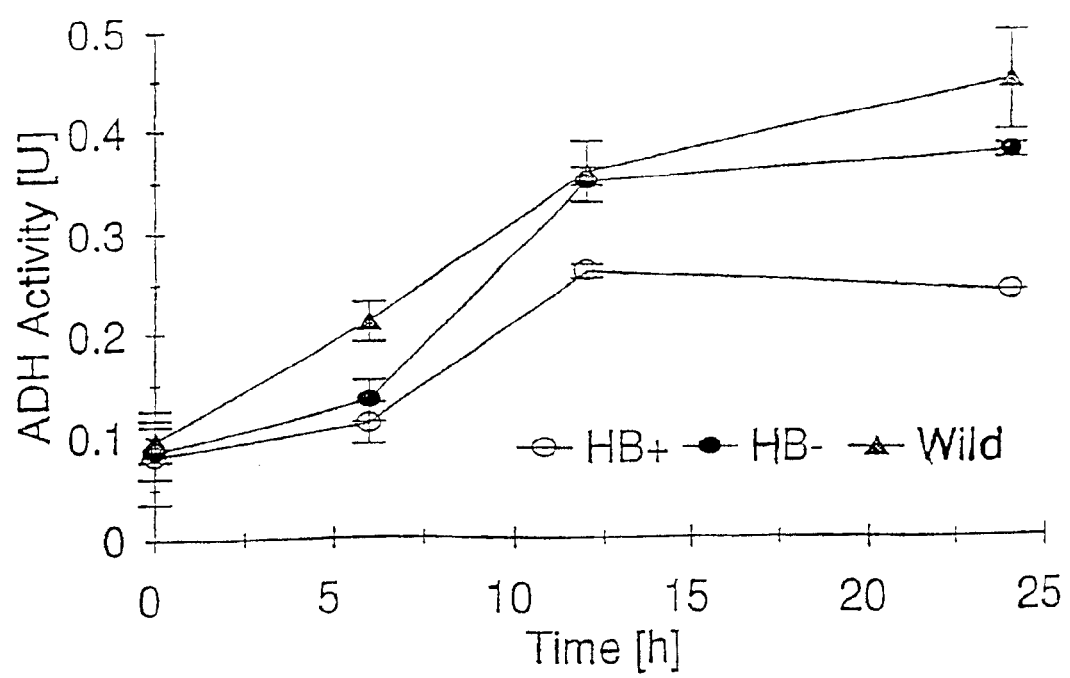
FIG. 7 is a graph of alcohol dehydrogenase activity in maize cells cultured under a nitrogen atmosphere.

An examination of alcohol dehydrogenase activity (ADH) in the cell lines showed that ADH increased in all three lines over the course of the experiments, but the ADH activity was significantly lower in the sense transformants ($HB^+$) than in antisense transformants ($HB^-$) or wild-type cells, as shown in FIG. 7. Fluorescein diacetate staining (Heslop-Harrison et al, 1984, *Theor Appl Genet* 67:367–375) showed no difference in the viability of the cell lines at the end of the incubation period. The reduced ADH activity, along with lower $CO_2$ evolution in $HB^+$ cells, likely reflects lower ethanolic fermentation rates, suggesting that a fermentative pathway may be the main source of carbon dioxide production in this system.

EXAMPLE VIII

Oxygen Uptake by Plant Cells

Figure 8:
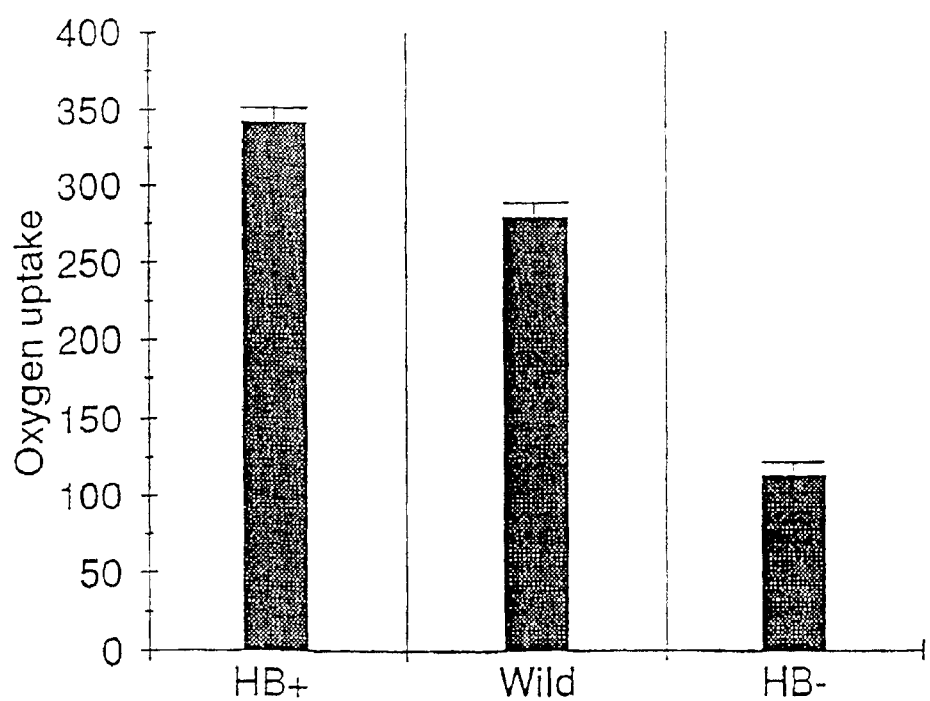
FIG. 8 is a bar graph of oxygen uptake by maize cells under low oxygen atmosphere.
Figure 9:
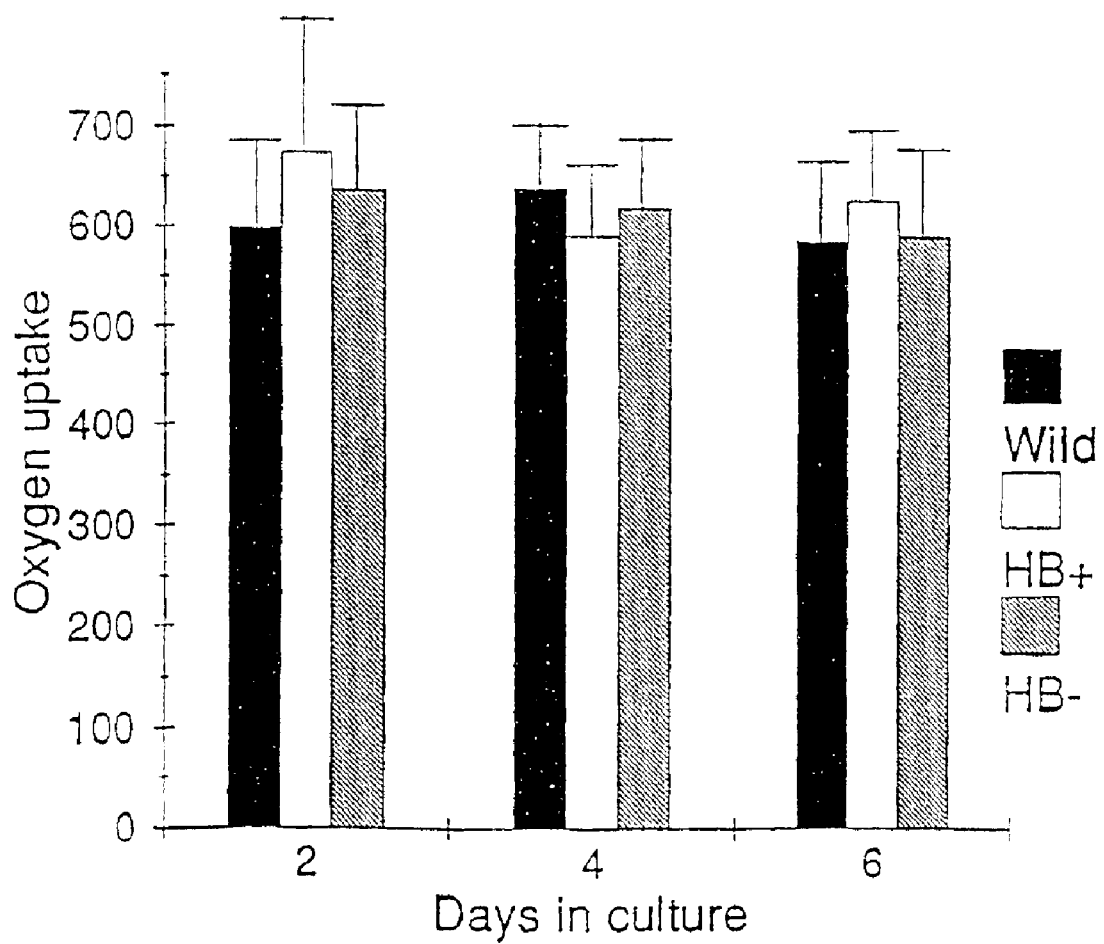
FIG. 9 is a bar graph of oxygen uptake by maize cells under normal air conditions.

As discussed above, the presence of nonsymbiotic hemoglobin clearly affects the energy status of maize cells under hypoxia. Furthermore, differences between the HB$^+$, wild type and HB$^-$ cells were observed only under the conditions of limited oxygen. To investigate the possibility that the observed differences may be due to the different abilities of the cell lines to utilize oxygen that is available in low concentrations, the oxygen uptake by the maize cells was measured under normal air conditions, shown in FIG. 9, and in medium equilibrated with a mixture of 2% $O_2$ and 98% $N_2$, shown in FIG. 8. Specifically, oxygen uptake was measured polarographically with an $O_2$ electrode. As can be seen, HB$^+$ cells were more efficient at oxygen uptake than the wild-type cells and much more efficient than the HB$^-$ cells. Specifically, the oxygen uptake by the HB$^+$ cells from the medium equilibrated with 2% oxygen was 55% of that of all three cell lines under normal air conditions, as shown in FIGS. 8 and 9. Furthermore, wild-type BMS and HB$^-$ cells grown at 2% $O_2$ exhibited $O_2$ uptake at 44% and 18% respectively of the oxygen uptake of the cell lines grown under normal conditions, as shown in FIGS. 8 and 9. These results clearly indicate that the rate of oxygen utilization by maize cells under low oxygen atmosphere depends on the presence of the non-symbiotic hemoglobin.

EXAMPLE IX

Plant Cell Growth After Exposure to Hypoxic Stress

Figure 10:
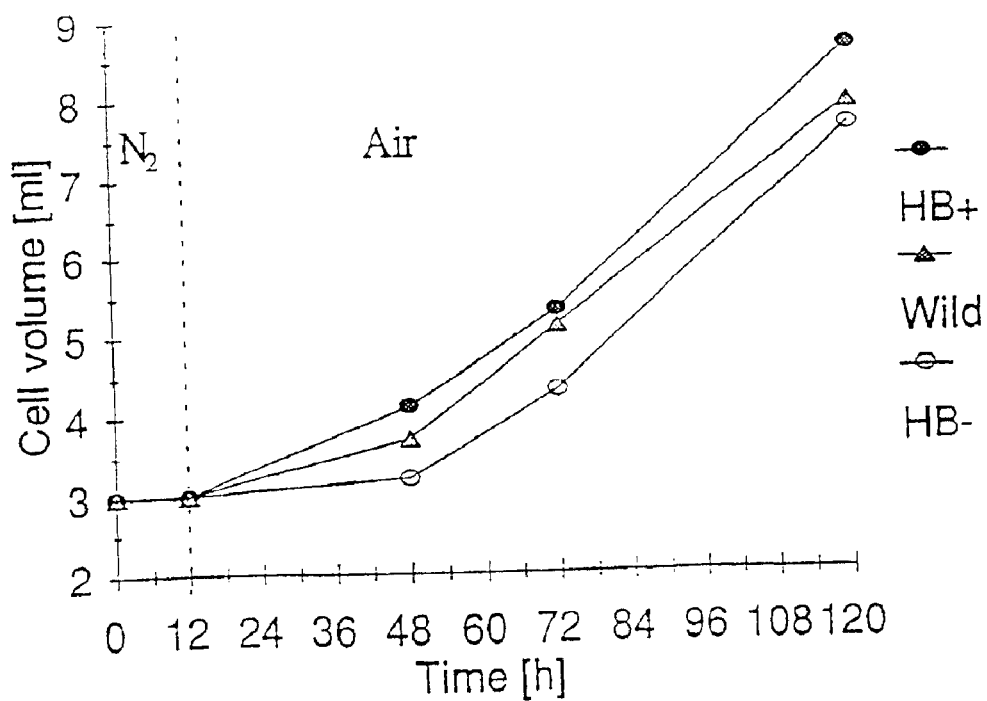
FIG. 10 is a graph of cell culture growth following hypoxic treatment.

The ability of the cell cultures to continue growth after exposure to hypoxic stress was also tested. Maize cell cultures were placed under the atmosphere. of nitrogen for 12 and 24 hours, then cells were harvested, transferred to a fresh medium and their growth was monitored by sedimented cell volume measurements, as shown in FIG. 10. Upon placement under the $N_2$ atmosphere, the cell growth of all three cell lines ceased, but resumed after transfer to the fresh medium and normal atmospheric conditions. However, while the HB$^+$ cell cultures resumed growth almost immediately after the transfer to normal air conditions, the HB$^-$ cells showed a 36 hour lag period before commencement of intensive growth. Furthermore, the growth of the wild-type cultures, during the first 36 hours after the transfer to normal conditions, was slower than that of HB$^+$ cells, as shown in FIG. 10. It is of note that after the initial 36 hour period, the growth rates of the three cell lines were almost identical. The differences in cell volume at each time point were most likely a result of the growth activity during this initial period. The culture re-growth after the 24 hour hypoxic exposure was the same for all three cell lines, as after the 12 hour treatment. The observed differences may be explained by different levels of cell survival under stress, and, depending on the cell line, the same cell volume could contain different numbers of growing cells. On the other hand, the increased growth rates of the HB$^{31}$ and the wild-type BMS cultures after a lag period, shown in FIG. 10, suggests a longer stress recovery period rather than cell death.

EXAMPLE X

Hemoglobin Expression in Germinating Barley

Figure 11:
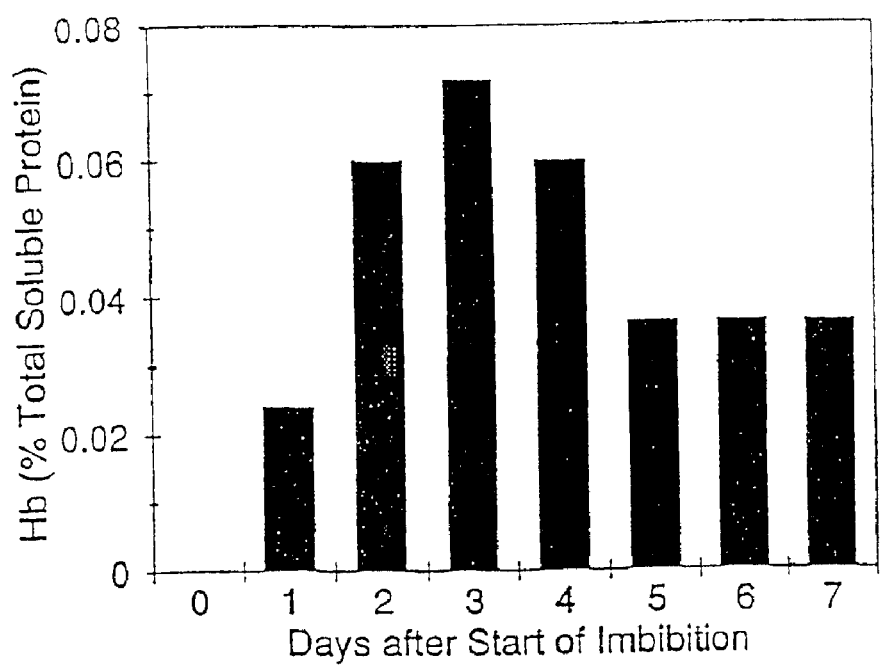
FIG. 11 is a bar graph of the amount of hemoglobin in crude extracts made from germinating barley seeds.

Polyclonal antibodies to purified recombinant barley hemoglobin were raised in rabbits and used to. investigate the expression of hemoglobin in monocotyledonous plants. Specifically, hemoglobin was shown to be expressed in whole seeds, as shown in FIG. 11, embryo-less half seeds and excised embryos during germination. The fact that hemoglobin was expressed in both embryo-less half seeds and excised embryos indicates that the gene is independently responsive to signals in both tissues and suggests that both the aleurone layer and the embryo may experience oxygen deficiencies during the imbibition process. In the excised embryo, hemoglobin was induced between 4 and 6. hours after imbibition. Since germination and the early stages of seedling growth are known to be periods of high metabolic demand (Bewley and Black, 1990, *Prog Nucleic Acid Res Mol Biol,* 38:165–193, incorporated herein by reference), this data is consistent with the proposed. concept that a demand on energy charge or ATP requirement is primarily responsible for hemoglobin induction (Nie and Hill, 1997, *Plant Physiol* 114:835–840). Major changes in ATP content of the embryos did occur within one hour after imbibition, which is consistent with previous reports. Protein hydration, protein synthesis. and nucleotide synthesis are among the first events of germination. These early -events, which consume large amounts of ATP, may well be a factor in the observed induction of hemoglobin synthesis at 4 to 6 hours after imbibition. However, induction occurs well before the major increase in α-amylase secretion, a period of high metabolic demand, and so the relationship between hemoglobin synthesis and energy availability needs further clarification.

In half seeds, there is an apparent induction of hemoglobin during imbibition, without the use of gibberellic acid to stimulate the synthesis of hydrolytic enzymes. Furthermore, isolated aleurone layers do not .show appreciable amounts of hemoglobin unless induced by anoxia using a nitrogen environment (Nie and Hill, 1997). The aleurones in these half-seeds may well be experiencing anoxia due to entrapment in the endosperm and seed coat.

Thus, to summarize, very little or no hemoglobin expression was observed in dry barley seeds but germination resulted in the expression of hemoglobin which peaked at 2–3 days after imbibition, as shown in FIG. 11. Furthermore, hemoglobin expression was also observed in maize, wheat, wild oat and *Echinochloa crus galli* seeds during germination. Dissection of tissues from the barley seedlings showed that most of the hemoglobin was expressed in the root and seed coat (aleurone layer), with very little in the coleoptile. Imbibition of half seeds or excised embryos resulted in the expression of hemoglobin. ATP measurements of barley embryos showed that ATP levels quickly increased after imbibition. α-Amylase activity was also determined in the embryos to correlate hemoglobin expression with a well-characterized germination response. The results demonstrate that hemoglobin expression is a normal consequence of germination.

Figure 13:
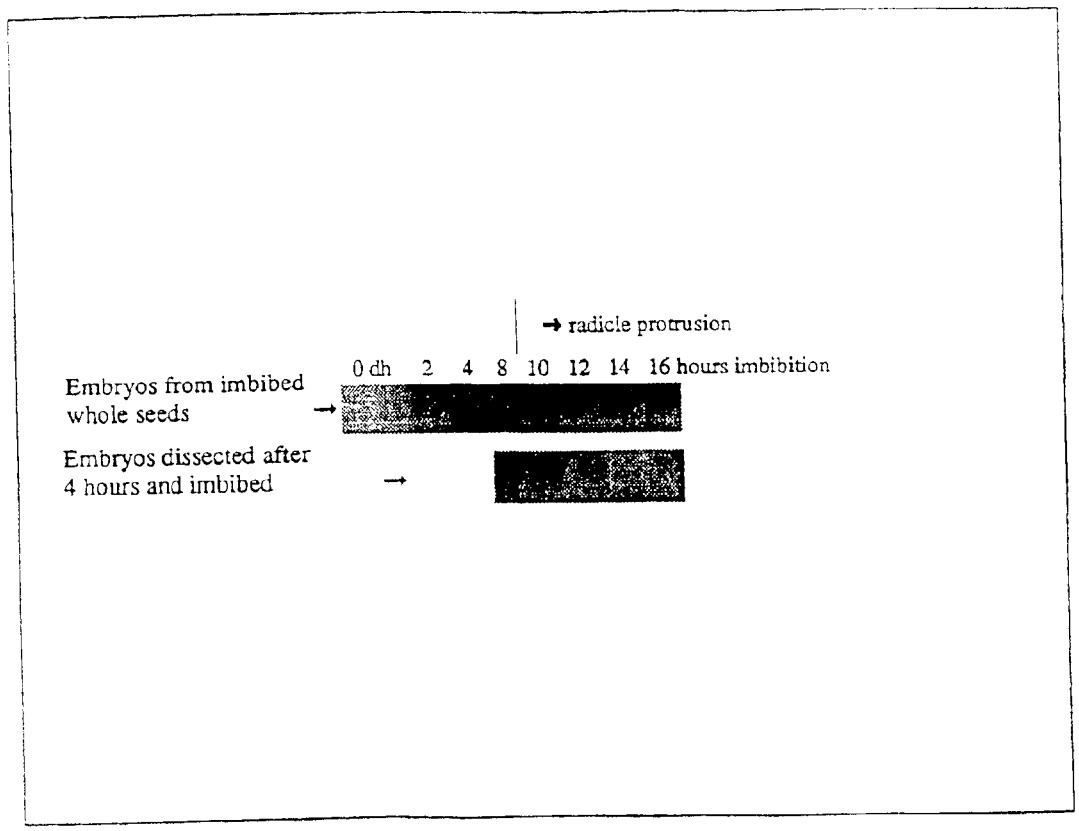
FIG. 13 is a Northern blot of RNA extracted over time from a germinating seedling.

In addition, whole barley seeds were imbibed for 16 hours at 22° C. Embryos were excised from the caryopis after 2, 4, 8, 10, 12, 14 and 16 hours imbibition. It was noted that radicle protrusion occurs after 8 hours. The embryos were ground in liquid nitrogen and RNA extracted for Northern analysis using an RNA probe transcribed from barley Hb cDNA. As can be seen in FIG. 13, it was found that no message was present in unimbibed seeds but was detectable after just two hours imbibition. Expression increased up until 8 hours when radicle emergence occurred. The amounts of message then decreased for the next 8 hours. These experiments show that hemoglobin expression occurs during germination. As such, it is clear that hemoglobin expression can be used as a marker for germination.

EXAMPLE XI

Construction of Bacterial Expression Constructs

A recombinant Hb cDNA-containing pUC19 construct (Duff et al, 1997) was used as the starting material. The Hb cDNA was excised from the pUC19 construct by digestion with the restriction enzymes EcoRI and HindIII. The insert was then ligated into the pPZ375 multiple cloning site between HindIII and EcoRI such that the coding sequence was in the correct reading frame.

EXAMPLE XII

Transformation and Screening of Recombinant *E. coli*

*Escherichia coli* DH5α cells were then transformed with the pPZ375-Hb construct according to the instructions for the Canadian Life Technologies subcloning efficiency competent cells, incorporated herein by reference. It is of note that in this instance Blue-White screening was unnecessary. *E. coli* cells were plated, screened and grown as previously described (Duff et al, 1997). Plasmid DNA was prepared from the cells using the small scale preparation protocol (Sambrook et al, 1989). The recombinant plasmid was then used to transform competent *Pseudomonas aeruginosa*, as described below.

EXAMPLE XIII

Preparation and Transformation of Competent *Pseudomonas aeruginosa*

100 ml of LB media in a 500 ml flask was inoculated with 1 ml of an overnight culture of *Pseudomonas aeruginosa* and grown for 2.5 hours to a cell density of approximately 108 cells/ml. Cells were harvested by centrifugation at 1000 g and then resuspended in 10 ml of Competency Buffer (0.15 M $MgCl_2$, 15% (v/v) glycerol; 1Q mM Pipes (Sigma), pH 7.0). Cells were incubated in an ice water bath for 5 minutes, pelleted at 1000 g, and resuspended in 10 ml of Competency Buffer. Cells were then incubated in an ice water bath for 20 minutes, pelleted at 1000 g, and resuspended in 10 ml of Competency Buffer. Cells were then frozen at −70° C. until used for transformation. DNA (approximately 0.2 μg of the recombinant plasmid) was used to transform 200 μl of competent *Pseudomonas aeruginosa* cells. Cells were incubated in an ice water bath for 60. minutes and heat shocked for 3 minutes at 37° C. while gently rocking the tube. Cells were placed in an ice water bath for 5 minutes. 0.5 ml of room temperature LB broth was added and the cells were incubated at 37° C. for 2.5 hours with no rotation. Cells were concentrated by centrifugation and plated on appropriate media.

EXAMPLE XIV

Electrophoresis and Bacterial Protein Immunoblotting

DNA agarose electrophoresis, protein acrylamide electrophoresis and protein immunoblotting was performed as previously described above.

EXAMPLE XV

Bacterial Growth and Treatment

*E. coli* was inoculated into four 400 ml cultures and grown for 3 hours. After 3 hours, $A_{600}$ was measured as an estimate of bacterial growth and then either air or nitrogen was bubbled through the media for 5 minutes and the flasks were sealed. The bacteria were grown for a further 6 hours after which the $A_{600}$ was determined for each flask as an estimate of bacterial growth. Similarly, *P. aeruginosa* was inoculated into four 400 ml cultures and grown for 3 hours using the same protocol as described above for *E. coli*,

EXAMPLE XVI

ATP Extraction and Assay

ATP was extracted and assayed according to standard procedures known in the art (Lowry and Passonneau, in *A Flexible System of Enzymatic Analysis* (1972, Academic Press: New York) pp 146–222, incorporated herein by reference).

EXAMPLE XVII

Expression of Barley Hb in *E. coli* and *P. aeruginosa*

Figure 12:
FIG. 12 is a Western blot of proteins from transformed and wild type P. aeruginosa. Each lane consisted of 80 μg of crude protein extract from P. aeruginosa cells and the blot was probed with affinity purified barley Hb antibodies. Lane 1 contains protein extracted from bacteria transformed with the Hb expression vector, whereas Lane 2 contains protein extracted from wild-type bacteria.

Untransformed *E. coli* cells and *E. coli* cells previously transformed with Hb cDNA were used (Duff et al., 1997). Western blot analysis confirmed that both *E. coli* (data not shown) and *P. aeruginosa* (FIG. 12) had been successfully transformed and were expressing significant amounts of Hb. Recombinant *E. coli* and *P. aeruginosa* were also visually more red than their wild type counterparts (data not shown). Levels of recombinant barley hemoglobin expressed in the two species of bacteria were roughly equal based on SDS-PAGE and protein immunoblot analysis.

EXAMPLE XVIII

Growth Rates of *E. coli* and *P. aeruginosa*

The $A_{600}$ measurements of 400 ml cultures of transformed and untransformed *E. coli* and *P. aeruginosa* grown under both aerobic and anaerobic conditions are shown in Table 2. *E. coli* containing the recombinant plasmid grew considerably slower than bacteria containing pUC19. There were no differences in growth between bacteria grown under air or anoxic conditions for *E. coli* containing either plasmid. *P. aeruginosa* containing the recombinant plasmid also grew somewhat slower than the bacteria containing pUC19. However, anoxic treatment virtually stopped the growth of both the wild type and recombinant obligate aerobic bacteria *P. aeruginosa*.

EXAMPLE XIX

ATP Levels in *E. coli* and *P. aeruginosa*

ATP levels from aerobically and anaerobically grown *E. coli* and *P. aeruginosa* are shown in Table 3. As can be seen, *E. coli* cells had the same total ATP regardless of whether or not they were expressing barley Hb or whether they were grown under aerobic or non-aerobic conditions. However, *P. aeruginosa* containing the recombinant barley Hb had significantly higher levels of ATP under both aerobic and non-aerobic conditions. These results are not surprising, given that *E. coli* readily adapts to grow in environments with limited oxygen. *P. aeruginosa*, on the other hand, is an obligate aerobe and is unable to grow in environments with limited oxygen. Furthermore, it is known that ATP levels and energy charge are directly related to the-metabolic state of an organism and that organisms with low ATP levels and energy charge are generally considered to be under stress or in a state of dormancy. Thus, the fact that *P. aeruginosa* containing nonsymbiotic hemoglobin has an improved energy status is evidence that the presence of this protein facilitates adaptation to low oxygen tension.

Discussion

Higher plant hemoglobins are cytoplasmic proteins (Wittenberg and Wittenberg, 1990). With this in mind, transformation constructs were designed for cytoplasmic expression of hemoglobin. Barley hemoglobin cDNA hybridizes to only one locus in barley and maize genomes (Taylor et al, Plant Mol Biol 24:853–862) and, therefore, -sense and antisense expression of this cDNA would not be expected to affect the expression of any other genes. It is of note that the polyclonal anti-hemoglobin antibody used was raised and titrated against recombinant barley hemoglobin. Furthermore, it is clear that there is over and under expression of hemoglobin in the transgenic cells.

The lack of effect of hemoglobin on cell growth and oxygen uptake under normal air-conditions likely reflects the fact that barley (Taylor et al, 1994) and maize hemoglobin genes are induced under conditions of limited oxygen availability, resulting in the protein having little effect when oxygen supplies are not impaired. The results, however, show clearly that the energy status of maize cells when oxygen is limiting is affected by the ability of the cells to produce hemoglobin. Total adenylates and ATP levels are maintained during the period of exposure to limiting oxygen when hemoglobin is constitutively expressed in the cells. Alternatively, when hemoglobin expression is suppressed by constitutive expression of antisense barley hemoglobin message, the cells are unable to maintain their energy status during oxygen limitation. In wild-type (BMS) cells, it would appear that the induction of native maize hemoglobin was sufficient to maintain the energy charge, but not the total adenylate pool. This is consistent with the observation that a decline in the adenylate pool has been noted during hypoxia in maize root tips (Saint-Ges et al, 1991, Eur J Biochem 200:477–482). Under limiting oxygen, plant cells turn their metabolism towards fermentation in order to oxidize NADH necessary to maintain glycolytic substrate phosphorylation. Lower alcohol dehydrogenase activity in HB$^+$ cells suggests that hemoglobin provides an alternative to potentially harmful fermentation. Specifically, carbon dioxide is produced by the HB$^+$ cells in lower amounts than by HB$^-$ and wild-type maize cells, reflecting lower ADH activity and suggesting that the ethanolic fermentation is the only source of $CO_2$. The dissociation constant of barley oxyhemoglobin is about 3 nM (Duff et al, 1997), indicating that oxyhemoglobin, acting alone, would be ineffective in providing oxygen to maintain mitochondrial respiratory processes. This is confirmed by the observation that Antimycin A has no effect on the ability of hemoglobin-containing cells in maintaining their energy status under low oxygen tensions. The results discussed above suggest that hemoglobin maintains energy status of. the cell by means different from mitochondrial oxidative phosphorylation , probably by facilitating glycolysis to generate ATP through substrate level phosphorylation.

It is of note that hemoglobins of barley (Taylor et al, 1994) and maize as well as Arabidopsis AHB1 (Trevaskis et al, 1997) are hypoxia inducible. Furthermore, it has been demonstrated that, in barley hemoglobin this is not due to a lack of oxygen per se, but in response to insufficient mitochondrial ATP synthesis. In addition, nonsymbiotic hemoglobins are expressed in metabolically active tissues such as roots (Taylor et al, 1994; Arredondo-Peter et al, 1997; Trevaskis, 1997), aleurone (Taylor et al, 1994), vascular tissues of leaves, stems and seedling cotyledons (Andersson et al, 1996, Proc Natl Acad Sci 93:5682–5687). Taken together, these data support a hypothesis that nonsymbiotic hemoglobins utilize available oxygen to maintain the cell's energy status in cells exposed to low oxygen tensions or other conditions that reduce cellular ATP levels. The very low dissociation constant of barley oxyhemoglobin makes it an ideal candidate for sequestering oxygen in low oxygen environments. Interaction with another compound, perhaps a flavoprotein, could create a complex capable of oxidizing NADH, in a manner analogous to Hmp protein of E. coli (Poole et al, 1996, Microbiology (Reading) 142:1141–1148). This would provide an efficient means of oxidatively regenerating NAD to support glycolysis, bypassing the fermentative route to ethanol.

The effects of expression. of sense and antisense hemoglobin on energy charge are reminiscent of hypoxic acclimation of plant tissues, for example, maize root tips, which develop a tolerance to short term anoxia if they have been acclimated by exposure to hypoxic conditions (Johnson et al, 1969, Plant Physiol 91:837–841). Specifically, acclimation is accompanied by increased energy charge (Hole et al, 1992, Plant Physiol 99:213–218) resulting from a sustained glycolytic rate compared to non-acclimated root tips (Xia and Saglio, 1992, Plant Physiol 100:40–46; Xia and Roberts, 1996, Plant Physiol 111:227–233). Similarly, winter cereals show increased survival to hypoxia caused by ice encasement if they have been acclimated by exposure to hypoxic conditions (Andrews and Pomeroy, 1983, Can J Bot 61:142–147). Acclimated plants maintain higher levels of adenylates and ATP during ice encasement, as a result of accelerated rates of glycolysis, than non-acclimated plants (Andrews and Pomeroy, 1989, Plant Physiol 91:1063–1068). Maximum induction of barley hemoglobin message occurs within 12 hours exposure to hypoxic conditions (Taylor et al, 1994), which is well within the time interval used for acclimation in the above examples. Furthermore, it has been shown that the expression of hemoglobin is not directly influenced by oxygen usage or availability but it is influenced by the availability of ATP in the tissue (Nie and Hill, 1997). This suggests that the increased survival of plants to anoxia as a result of hypoxic acclimation is a consequence of hemoglobin gene expression induced by declining ATP levels during acclimation.

From an evolutionary standpoint, it has been suggested that nonsymbiotic hemoglobins represent one. of the more ancient forms of plant hemoglobins (Andersson et al, 1996). Evidence presented here adds credence to this idea. Since early life on earth existed in oxygen-poor environments, the presence of a hemoglobin capable of utilizing oxygen. at low oxygen tensions would have provided an evolutionary advantage to an organism. Oxygen produced during photosynthesis and retained as oxyhemoglobin would provide a source of oxygen to oxidize NADH, maintaining a high glycolytic flux during darkness to provide ATP for cell growth and development.

The high oxygen avidity of hemoglobin (Arredondo-Peter et al, 1997; Duff et al, 1997; Trevaskis et al, 1997) argues against hemoglobin functioning to facilitate diffusion of oxygen. Because the hemoglobin will be induced intracellularly in a highly reductive environment with low energy charge it is possible that hemoglobin functions as an electron transport protein similar to cytochrome c. Further work is now being carried out to more closely examine the potential effect of oxygen limitation and hemoglobin expression during germination.

The function of this enigmatic protein is still far from certain. We have observed hemoglobin gene expression (or increases in hemoglobin expression) unequivocally in at least 4 cases: (1) in intact whole seeds during germination; (2) in excised embryos and embryo-less half seeds imbibed in water; (3) in aleurone layers which have been stressed by a low oxygen environment or respiratory inhibitors (Nie and Hill, 1997); and (4) in barley roots after flooding (Taylor et al, 1994). In every situation, it is likely that the ATP requirement of the cell exceeds the ATP supply either because of low oxygen supply (such as is the case of the flooded plants or stressed seed tissue) or due to high metabolic rates (such as likely to be the case during germination). Hemoglobin expression seems to be both a normal event during seed germination as well as an adaptation of plants to low oxygen environments.

As. discussed above, the results obtained from expression of Hb in bacterial cells are reminiscent of maize suspension cells where it was hypothesized that Hb might be involved in maintaining the level of ATP through the involvement of a pathway other than oxidative phosphorylation. It seems reasonable to conclude that given the similarity of results that a similar mechanism might be occurring in *P. aeruginosa* but not *E. coli*. As discussed above, this is likely due to the fact that *E. coli* adapts readily to grow under conditions of limited oxygen, whereas *P. aeruginosa* is an obligate aerobe and does not normally grow under conditions of limited oxygen. However, the fact that this phenomenon is seen in organisms as diverse as plants and aerobic bacteria further suggests that whatever the function of the nonsymbiotic plant hemoglobin is, it may be widely represented in nature and may have evolved from a very ancient and fundamental form of oxidative metabolism which evolved before mitochondrial oxidative phosphorylation. This final conclusion is suggested by the fact that Hb can bind oxygen at levels far lower than most other oxygen binding proteins (especially cytochrome C and the alternative oxidase) and may have evolved when oxygen levels in the atmosphere were much lower.

As will be apparent to one knowledgeable in the art, for expressing Hb in a variety of host organisms, expression vectors may be constructed containing Hb linked to a host-specific promoter. Furthermore, the expression vector may contain a selectable marker functional in the specific host for selecting transformants. In this manner, a variety of expression vectors may be constructed for use in a variety of host organisms. Transgenic or recombinant organisms containing these vectors will have increased tolerance to hypoxic conditions, lower levels of fermentation products and increased oxygen uptake. More specifically, plants containing the Hb expression vector described above engineered for expression in a given plant will have improved agronomic properties, such as, for example, germination, seedling vigour, reduced cellular levels of fermentation products, increased oxygen uptake, and increased tolerance to hypoxic conditions.

Furthermore, given that the effect of nonsymbiotic hemoglobin on cell energy status is seen in both bacteria and plants, it seems likely that this phenomenon is universal. This would in turn mean that nonsymbiotic hemoglobins have potential applications in a number of medical procedures. For example, skin cells from burn victims are frequently cultured for transplantation back to the burn victim. Given that oxygen supply is a limiting factor for growth and survival of the transplanted skin grafts, skin cells transfected with nonsymbiotic hemoglobin may possess improved growth and survival. Similarly, oxygen supply is also a limiting factor in other medical procedures, for example, organ transplants. That is, it is likely that organs possessing nonsymbiotic hemoglobins may have enhanced survival following transplant.

As is apparent to one knowledgeable in the art, other oxygen binding proteins displaying a low dissociation constant for oxygen may be used in place of Hb in the above-described expression vectors.

Furthermore, as discussed above, the expression of hemoglobin occurs during seedling germination. As such, expression of hemoglobin can be used as a marker for germination. In addition, as discussed above, hemoglobin expression is clearly related to seedling vigour. As such, levels of hemoglobin expression at the time of germination can be used for selecting seeds for breeding.

Since various modifications can be made in our invention as herein above described, and many apparently widely different embodiments of same made within the spirit and scope of the claims without department from such spirit and scope, it is intended that all matter contained in the accompanying specification shall be interpreted as illustrative only and not in a limiting sense.

TABLE 1

Energy charge and total adenylates in maize cells before and after exposure to a nitrogen atmosphere for 12 hours. Results are expressed as nmol per g fresh weight. Maximum SE (n = 3) was 5%.

| Cell Line | Energy Charge | | Total adenylates (nmol per g fresh weight) | |
| --- | --- | --- | --- | --- |
| | Air | Nitrogen | Air | Nitrogen |
| $HB^+$ | 0.93 | 0.93 | 96 | 92 |
| Wild | 0.94 | 0.93 | 94 | 61 |
| $HB^-$ | 0.91 | 0.73 | 99 | 59 |

TABLE 2

$A_{600}$ measurements of transformed and untransformed *E. coli* and *P. aeruginosa* cells grown aerobically and anaerobically. Measurements are the averages of two separate determinations which did not vary by more than 15%.

| | *E. coli* | | *P. aeruginosa* | |
| --- | --- | --- | --- | --- |
| | Wild type | +Hb | Wild type | +Hb |
| 3 hr $O_2$ | 0.044 | 0.040 | 0.098 | 0.059 |
| 9 hr $O_2$ | 0.147 | 0.110 | 1.392 | 1.074 |
| 3 hr $O_2$ + 6 hr $N_2$ | 0.144 | 0.102 | 0.141 | 0.074 |

TABLE 3

ATP measurements of transformed and untransformed *E. coli* and *P. aeruginosa* cells grown aerobically and anaerobically. Measurements are the results of duplicate assays from 3 separate experiments. Standard error was in all cases no greater than 10%.

| | *E. coli* | | *P. aeruginosa* | |
| --- | --- | --- | --- | --- |
| | Wild type | +Hb | Wild type | +Hb |
| 9 hr $O_2$ | 0.019 | 0.019 | 0.019 | 0.025 |
| 3 hr $O_2$ + 6 hr $N_2$ | 0.018 | 0.019 | 0.011 | 0.018 |

What is claimed is:

1. A method of increasing a plant's tolerance to hypoxic conditions, comprising transforming a plant with an expression system comprising a nucleic acid molecule encoding a plant nonsymbiotic hemoglobin, wherein the plant exhibits increased tolerance to hypoxic conditions as compared to a plant that has not been transformed with a nucleic acid molecule encoding a plant nonsymbiotic hemoglobin.

2. The method according to claim 1, wherein the plant nonsymbiotic hemoglobin is barley nonsymbiotic hemoglobin.

3. The method according to claim 1, wherein the plant exhibits improved germination under hypoxic conditions, as compared to a plant that has not been transformed with a nucleic acid molecule encoding a plant nonsymbiotic hemoglobin.

4. The method according to claim 1, wherein the plant exhibits improved seedling vigour under hypoxic conditions, as compared to a plant that has not been transformed with a nucleic acid molecule encoding a plant nonsymbiotic hemoglobin.

5. The method according to claim 1, wherein the plant exhibits reduced cellular levels of ethanolic fermentation products under hypoxic conditions, as compared to a plant that has not been transformed with a nucleic acid molecule encoding a plant nonsymbiotic hemoglobin.

6. The method according to claim 1, wherein the plant exhibits increased oxygen uptake under hypoxic conditions, as compared to a plant that has not been transformed with a nucleic acid molecule encoding a plant nonsymbiotic hemoglobin.

7. The method according to claim 1, wherein the hypoxic conditions are related to one or more conditions selected from the group consisting of ice encasement, flood, and impacted soil.

8. The method according to claim 1, wherein the plant exhibits increased ability to maintain total adenylates under hypoxic conditions, as compared to a plant that has not been transformed with a nucleic acid molecule encoding a plant nonsymbiotic hemoglobin.

9. The method of claim 1, wherein the expression system further comprises a control sequence operably linked to said nucleic acid molecule.

10. The method of claim 9, wherein the control sequence is a strong constitutive promoter.

11. The method of claim 9, wherein the control sequence is a host-specific promoter.

12. The method of claim 1, wherein the plant nonsymbiotic hemoglobin is a rice nonsymbiotic hemoglobin.

13. The method of claim 1, wherein the plant nonsymbiotic hemoglobin is an Arabidopsis nonsymbiotic hemoglobin.

14. The method of claim 1, wherein the plant nonsymbiotic hemoglobin is a maize nonsymbiotic hemoglobin.

15. The method of claim 1, wherein the plant is a maize plant.

16. The method of claim 15, wherein the expression system further comprises a maize ubiquitin promoter.

17. The method of claim 1, wherein the expression system further comprises a selectable marker.

18. A plant having increased tolerance to hypoxic conditions transformed in accordance with the method of claim 1.

19. The plant of claim 18, wherein the plant expresses plant nonsymbiotic hemoglobin at an elevated level under hypoxic conditions as compared to a plant that has not been transformed with an expression system comprising a nucleic acid molecule expressing a plant nonsymbiotic hemoglobin.

20. The plant of claim 19, wherein the plant expresses plant nonsymbiotic hemoglobin under hypoxic conditions at a level ten times higher than that of a plant that has not been transformed with an expression system comprising a nucleic acid molecule expressing a plant nonsymbiotic hemoglobin.

* * * * *